US00PP36714P3

(12) United States Plant Patent
Stevens et al.

(10) Patent No.: US PP36,714 P3
(45) Date of Patent: Jun. 3, 2025

(54) PISTACHIO HYBRID ROOTSTOCK NAMED '19PaPi-SY'

(50) Latin Name: ***Pistacia atlantica* x *Pistacia integerrima***
Varietal Denomination: 19PaPi-SY

(71) Applicant: Sierra Gold Nurseries, Inc., Yuba City, CA (US)

(72) Inventors: Micah Stevens, Yuba City, CA (US); Reid Robinson, Yuba City, CA (US); Charles Brannon, Yuba City, CA (US)

(73) Assignee: Sierra Gold Nurseries, Inc., Yuba City, CA (US)

( * ) Notice: Subject to any disclaimer, the term of this patent is extended or adjusted under 35 U.S.C. 154(b) by 133 days.

(21) Appl. No.: 18/230,583

(22) Filed: Aug. 4, 2023

(65) Prior Publication Data

US 2025/0048945 P1 Feb. 6, 2025

(51) Int. Cl.
*A01H 5/08* (2018.01)
*A01H 5/10* (2018.01)
*A01H 6/00* (2018.01)

(52) U.S. Cl.
USPC ..... Plt./152
CPC ..... *A01H 5/10* (2013.01); *A01H 6/00* (2018.05)

(58) Field of Classification Search
USPC ..... Plt./152
See application file for complete search history.

*Primary Examiner* — Susan McCormick Ewoldt
(74) *Attorney, Agent, or Firm* — Michelle Bos Legal LLC

(57) ABSTRACT

A new and distinct pistachio tree named '19PaPi-SY' developed for use as a rootstock and notable for its vigor, amenability to in vitro propagation, asphyxia tolerance and compatibility with *Pistacia vera* scions.

4 Drawing Sheets

Latin name: *Pistacia atlantica* x *Pistacia integerrima.*
Variety denomination: '19PaPi-SY'.

BACKGROUND OF THE VARIETY

'19PaPi-SY' is a new and distinct pistachio tree developed for use as a rootstock. '19PaPi-SY' was selected from among seedlings obtained from a controlled cross of female parent *Pistacia atlantica* (not patented) and male parent *Pistacia integerrima* (not patented) carried out at Yuba City, California. The '19PaPi-SY' pistachio tree was observed to be more vigorous than standard pistachio rootstock 'UCB-1' (not patented) and was selected for propagation and further observation in 2020. The first asexual propagation of the variety was carried out by in vitro propagation in 2020 at Yuba City, California. The variety has since been asexually reproduced through successive generations and has been observed to remain true to type.

BRIEF DESCRIPTION OF THE VARIETY

'19PaPi-SY' was first selected for its vigor as compared to 'UCB-1' pistachio rootstock. A molecular genetic marker associated with '19PaPi-SY' is an indicator of broad environmental adaptability of increased vigor. A comparison of '19PaPi-SY' and 'UCB-1' to the industry standard is set forth in Table 1 below.

TABLE 1

Comparison of '19PaPi-SY' and 'UCB-1' to Industry Standard

| | Relative Size to Industry Standard $2^{nd}$ Leaf | | Relative Size to Industry Standard $3^{rd}$ Leaf | |
|---|---|---|---|---|
| Rootstock | Rootstock | Scion | Rootstock | Scion |
| 19PaPi-SY | 126% | 138% | 121% | 114% |
| UCB-1 | 101% | 129% | 83% | 94% |
| Industry Standard | 100% | 100% | 100% | 100% |

'19PaPi-SY' has been found to be more amenable to in vitro propagation than 'UCB-1', with an in vitro multiplication rate of about 133% of the 'UCB-1' multiplication rate. Asphyxia tolerance in '19PaPi-SY' exceeds that of 'UCB-1' and 'P.N.1-15' (U.S. Plant Pat. No. 14,706) commercial pistachio rootstocks. '19PaPi-SY' is further useful as a rootstock due to its scion compatibility with *Pistacia vera* edible kernel pistachio varieties.

BRIEF DESCRIPTION OF THE PHOTOGRAPHS

Figure 1:
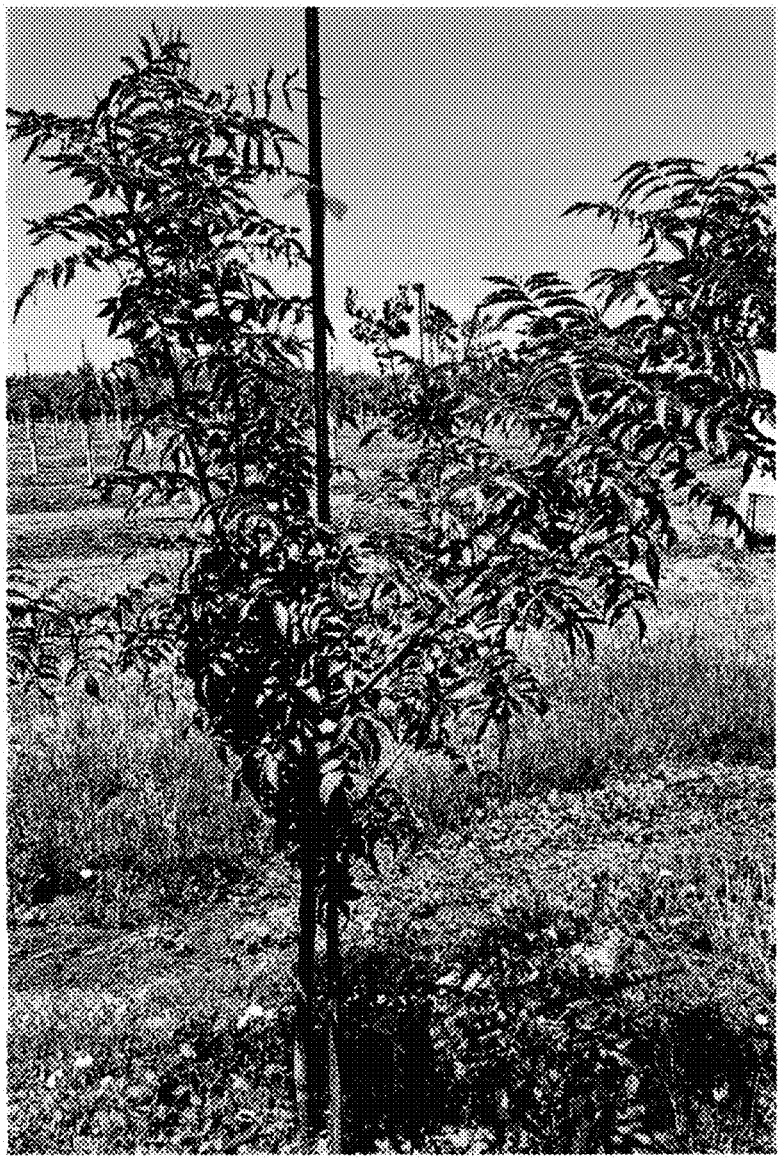
Figure 2:
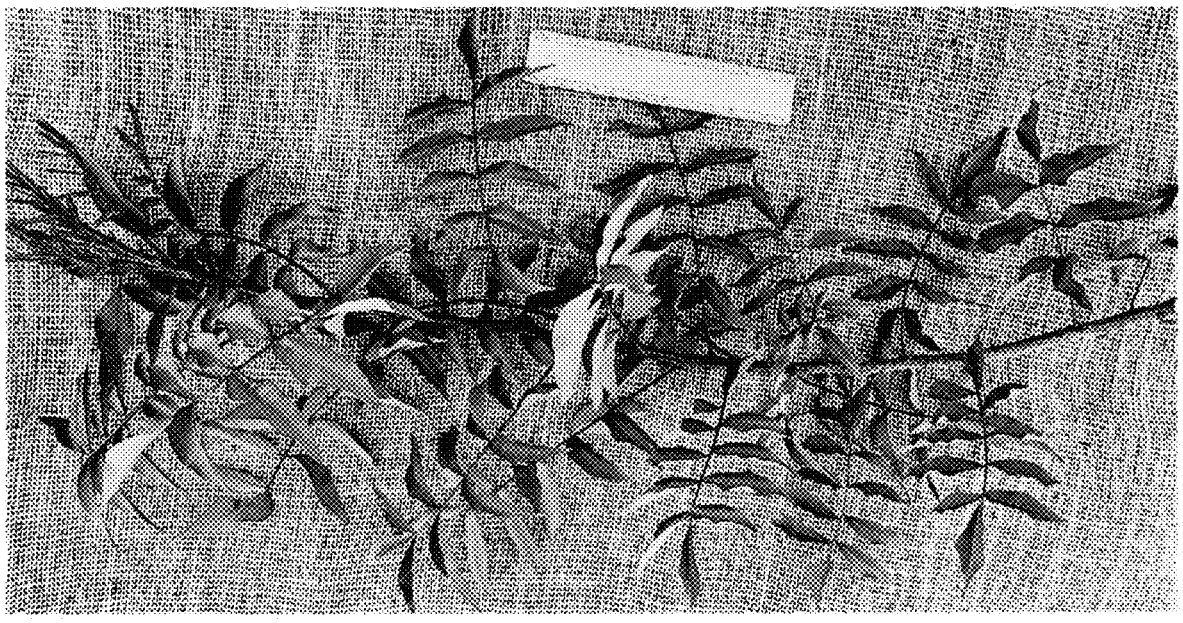
Figure 3:
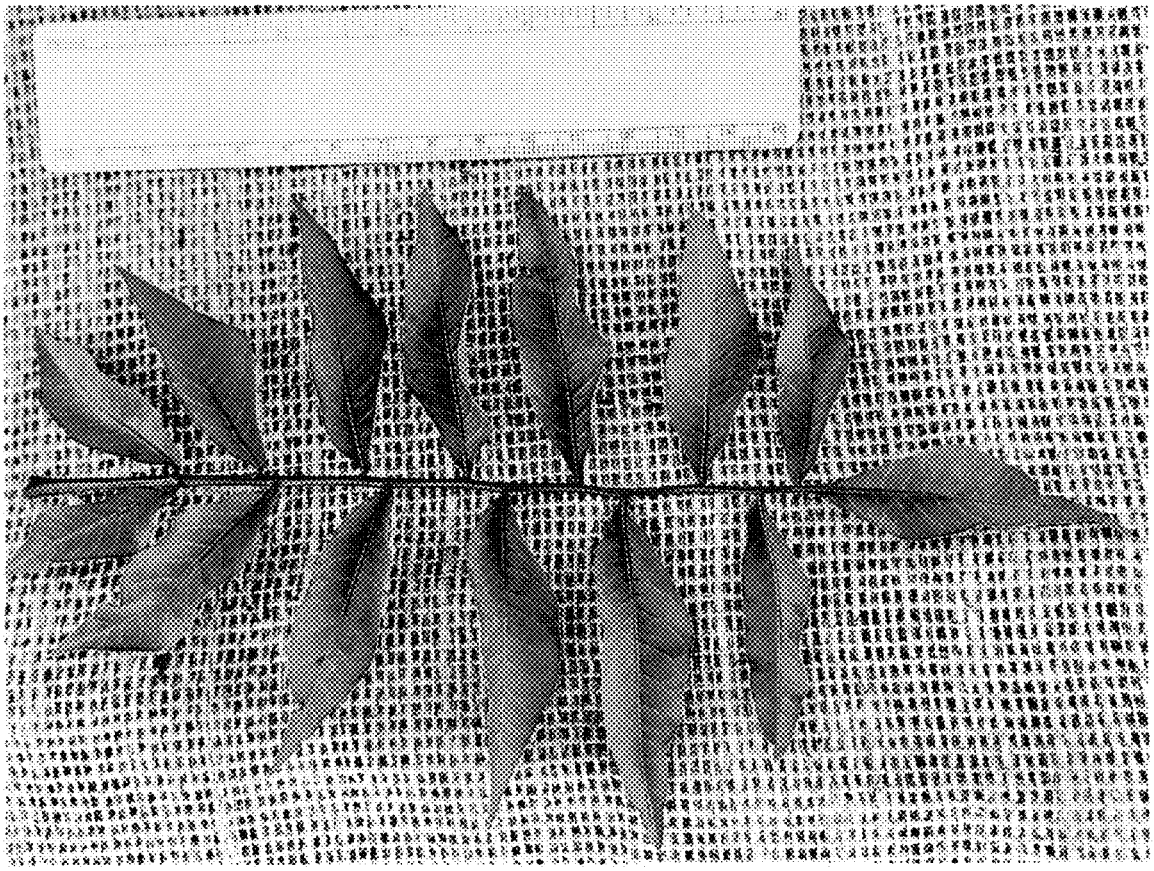
Figure 4:
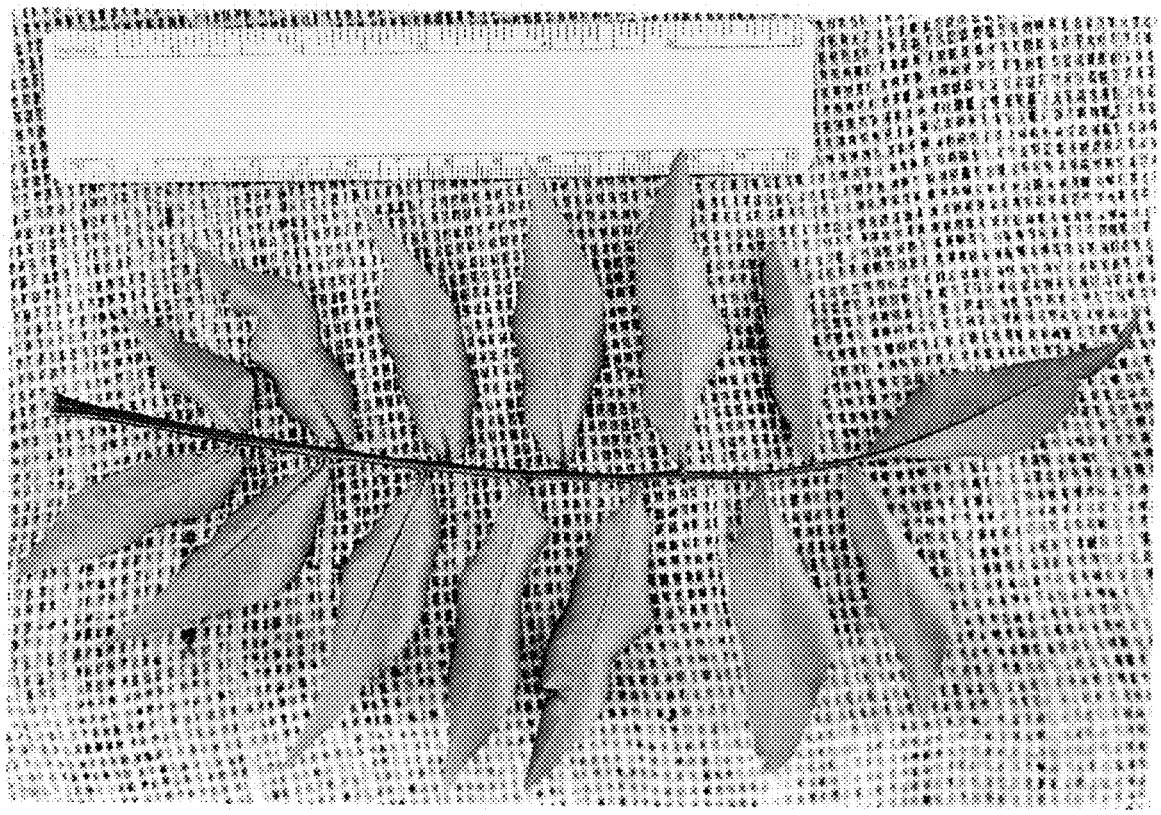

FIG. 1 shows a tree of the claimed variety;
FIG. 2 shows a branch and leaves of the claimed variety;
FIG. 3 shows the upper surface of leaves of the claimed variety; and
FIG. 4 shows the lower surface of leaves of the claimed variety.

DETAILED BOTANICAL DESCRIPTION OF THE VARIETY

The following-detailed botanical description is based on observations made at Yuba City, California during the 2023 growing season of 3-year-old trees grown on their own roots. All colors are described according to The R.H.S. Colour Chart (Royal Horticultural Society, London, $6^{th}$ edition). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Height*.—1.8 m.
*Trunk diameter at* 20 *cm above the soil*.—24.6 mm.
*Bark texture*.—Slightly rough.
*Bark color*.—Grey-brown 199C.
*Lenticel length*.—1.9 cm to 2.0 mm.
*Lenticel width*.—<1 mm.
*Lenticel shape*.—Flat.
*Lenticel color*.—Greyed-orange 165C.
*Lenticel density per* $cm^2$.—0 to 6.

One year old shoot:

*Length*.—70 cm to 79 cm.
*Diameter*.—8.0 mm to 9.1 mm.
*Pubescence*.—Absent.
*Color*.—Greyed-red 178A.
*Lenticel length*.—<1 mm.
*Lenticel width*.—<1 mm.
*Lenticel shape*.—Round.
*Lenticel color*.—Greyed-orange 165B.
*Lenticel density per* $cm^2$.—0 to 8.

Leaves:

*Shape*.—Alternate, even-pinnately compound.
*Length*.—18.1 cm to 25.6 cm.
*Width*.—12.1 cm to 15.6 cm.
*Length/width ratio*.—1.2:1.
*Leaflet length*.—7.1 cm to 8.2 cm.
*Leaflet width*.—1.8 cm to 2.6 cm.
*Blade margin*.—Entire.
*Apex shape*.—Acute.
*Base shape*.—Attenuate.
*Color of upper surface*.—Green NN137B.
*Color of lower surface*.—Yellow-green 146B.
*Attitude in relation to shoot*.—Outward.

Petiole:

*Length*.—3.8 cm.
*Diameter*.—3 mm to 4 mm.
*Color*.—Greyed-red 178A.

Disease resistance/susceptibility: Tolerant of *Verticillium* wilt.

Pest resistance/susceptibility: None observed to date.

The invention claimed is:

1. A new and distinct pistachio tree named '19PaPi-SY' substantially as illustrated and described herein.

* * * * *